(12) United States Patent
Meziane

(10) Patent No.: US 12,295,738 B2
(45) Date of Patent: May 13, 2025

(54) METHOD AND DEVICE FOR MEASURING THE STATUS OF OXIDATIVE STRESS IN A BIOLOGICAL MATRIX

(71) Applicant: Smail Meziane, Neuves-Maisons (FR)

(72) Inventor: Smail Meziane, Neuves-Maisons (FR)

( * ) Notice: Subject to any disclaimer, the term of this patent is extended or adjusted under 35 U.S.C. 154(b) by 960 days.

(21) Appl. No.: 17/298,313

(22) PCT Filed: Nov. 28, 2019

(86) PCT No.: PCT/FR2019/052835
§ 371 (c)(1),
(2) Date: Jul. 16, 2021

(87) PCT Pub. No.: WO2020/109736
PCT Pub. Date: Jun. 4, 2020

(65) Prior Publication Data
US 2022/0031230 A1    Feb. 3, 2022

(30) Foreign Application Priority Data

Nov. 28, 2018 (FR) ...................................... 1871986

(51) Int. Cl.
*A61B 5/00*     (2006.01)
*A61B 5/1477*   (2006.01)
*G01N 27/403*   (2006.01)
*G01N 27/416*   (2006.01)

(52) U.S. Cl.
CPC ............ *A61B 5/443* (2013.01); *A61B 5/1477* (2013.01); *G01N 27/4035* (2013.01); *G01N 27/4166* (2013.01)

(58) Field of Classification Search
CPC .................. A61B 5/443; A61B 5/1477; G01N 27/4035; G01N 27/4166; G01N 2333/00
See application file for complete search history.

(56) References Cited

U.S. PATENT DOCUMENTS

| 2008/0294026 A1* | 11/2008 | Arbault .................. A61B 5/442 600/345 |
| 2017/0241945 A1* | 8/2017 | Kumar .................. A61B 5/1477 |
| 2021/0364464 A1* | 11/2021 | Heikenfeld ............ C12Q 1/001 |

FOREIGN PATENT DOCUMENTS

| FR | 2895226 B1 | 3/2008 | |
| FR | 3043208 B1 | 12/2017 | |
| WO | WO-2007036483 A1 * | 4/2007 | ............. A61B 5/442 |
| WO | WO-2011064265 A1 * | 6/2011 | ......... A61B 5/14539 |
| WO | 2017/077237 A1 | 3/2017 | |

OTHER PUBLICATIONS

Bist et al., Electrochemiluminescent Array to Detect Oxidative Damage in ds-DNA using [Os(bpy)2(phen-benz-COOH2+/Nafion/Graphene Films, ACS Sens., vol. 1, No. 3, (2016), 17 pages.

(Continued)

*Primary Examiner* — Luan V Van
*Assistant Examiner* — Shizhi Qian
(74) *Attorney, Agent, or Firm* — TraskBritt

(57) ABSTRACT

Methods and devices for measuring the status of oxidative stress on the surface or in a biological matrix involve use of at least one compound selected from NADH, NADPH, Cyt C ($Fe^{2+}$) or $H_2O_2$.

11 Claims, 1 Drawing Sheet

(56) References Cited

OTHER PUBLICATIONS

Brainina et al., Noninvasive Method of Determining Skin Antioxidant/Oxidant Activity: Clinical and Cosmetics applications, Analytical Bioanytical Electrochemistry, (Oct. 2013), 16 pages.
International Search Report for International Application No. PCT/FR2019/052835 dated Mar. 24, 2020, 3 pages.
International Written Opinion for International Application No. PCT/FR2019/052835 dated Mar. 24, 2020, 7 pages.
Kohen et al., Reducing Equivalents in the Aging Process, Archives of Gerontology and Geriatrics, vol. 24, Issue 2, (Mar.-Apr. 1997), pp. 103-123.
Prieto-Simon et al., Electrochemical Biosensors as a Tool for Antioxidant Capacity Assessment, Sensors and Actuators B: Chemical, vol. 129, Issue 1, (Jan. 29, 2008), pp. 459-466.

* cited by examiner

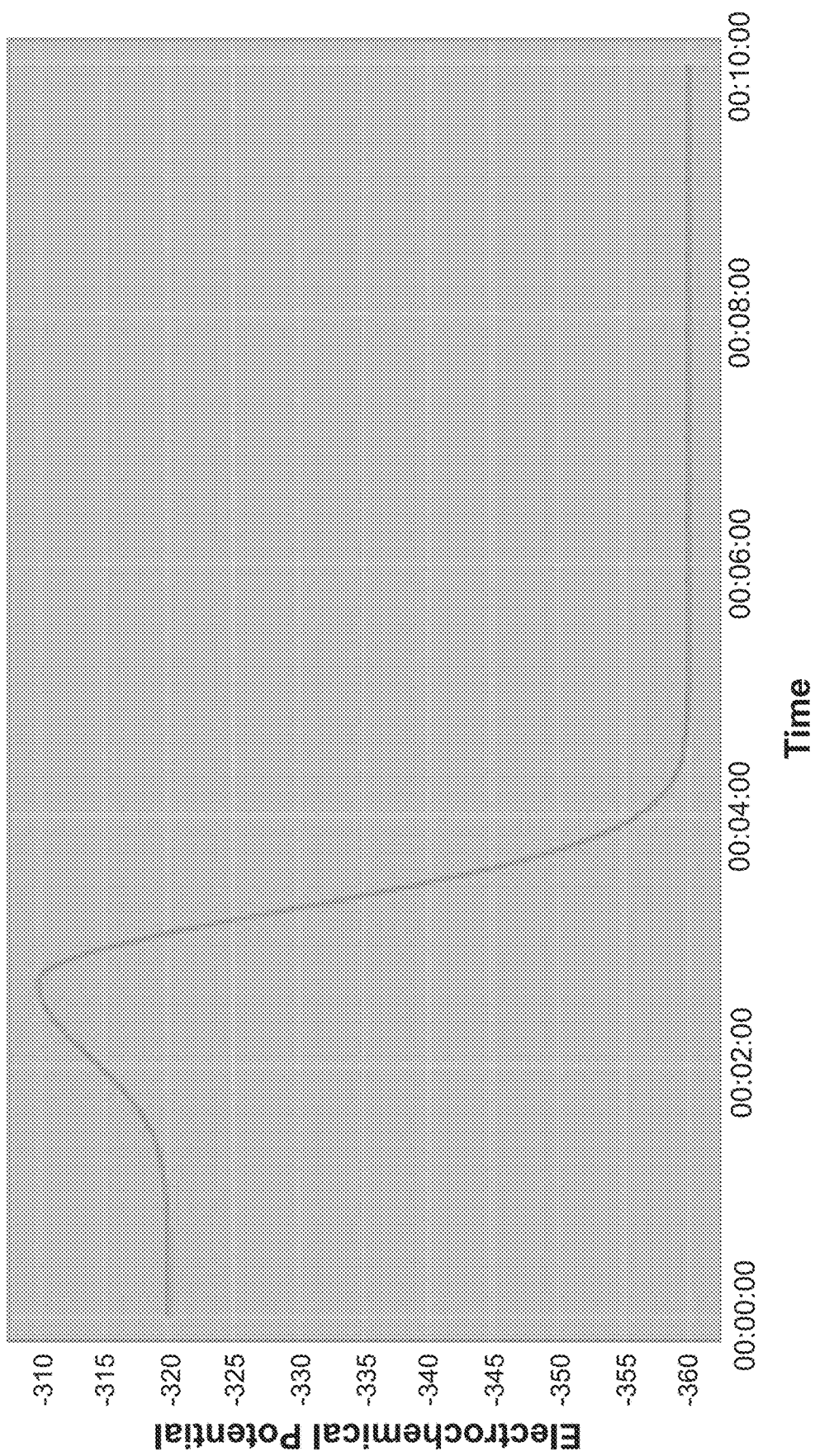

METHOD AND DEVICE FOR MEASURING THE STATUS OF OXIDATIVE STRESS IN A BIOLOGICAL MATRIX

CROSS-REFERENCE TO RELATED APPLICATIONS

This application is a national phase entry under 35 U.S.C. § 371 of International Patent Application PCT/FR2019/052835, filed Nov. 28, 2019, designating the United States of America and published as International Patent Publication WO 2020/109736 A1 on Jun. 4, 2020, which claims the benefit under Article 8 of the Patent Cooperation Treaty to French Patent Application Serial No. 1871986, filed Nov. 28, 2018.

TECHNICAL FIELD

The present disclosure relates to the field of methods and devices for measuring the status of oxidative stress on the surface or in a biological matrix. More particularly, it relates to a method for measuring the status of oxidative stress of a biological matrix involving at least one compound AB chosen from NADH, NADPH, Cyt C ($Fe^{2+}$) or $H_2O_2$.

BACKGROUND

Oxidative stress corresponds to a disruption of the balance between the production of free radicals, which are oxidizing species, and the ability of the body's protective mechanisms, represented by antioxidants, to neutralize these free radicals before they cause damage to the matrix.

Regarding living organisms more particularly, and, in particular, the human species, oxidative stress is suspected of being at the origin of cellular aging and of numerous pathologies, such as Alzheimer's and Parkinson's diseases in particular.

As a result, certain manufacturers in various sectors, such as cosmetics, food processing and medicine, are seeking to develop new molecules or new compounds with antioxidant properties, with the aim of reducing the effects of oxidative stress. These antioxidant compounds are also incorporated into certain food products, pharmaceuticals, nutraceuticals or cosmetic compositions, in order to increase their storage time while having a beneficial effect on the consumer health.

In this context, it is advantageous to be able to reliably and reproducibly measure the effects on an organism of the administration of an antioxidant substance or, on the contrary, of an oxidizing substance.

Patent application WO2017077237A1 is known, which presents a device and a method for measuring the total antioxidant and oxidative capacity of any matrix. The measurements are carried out by reacting a mediator system comprising a compound A and a compound B, which are different from one another, with the matrix to be tested, then by measuring the electrochemical potential of the mediator system.

BRIEF SUMMARY

A mediator system has been developed that is particularly suitable for biological matrices composed of a single compound AB available in two forms A and B. Form A can react and/or form complexes with an antioxidant and Form B can react and/or form complexes with an oxidant, but Forms A and B do not interact with each other.

The disclosure relates to the use of at least one compound AB that is non-toxic to the skin chosen from NADH, NADPH, Cyt C ($Fe^{2+}$) or $H_2O_2$ for measuring the status of oxidative stress of a biological matrix, characterized in that the at least one compound is available in two forms AB that do not interact with each other, and that are capable of interacting and/or forming complexes respectively with an antioxidant and an oxidant present on the surface or in the biological matrix.

Advantages of the Disclosure

The groups of compounds A and B according to the disclosure have the advantage of being molecules that are non-toxic for the skin, unlike the compounds used in the prior art such as ferric ammonium sulphate, cerium or iodine monobromide. Thus, the mixtures of compounds A and B prove to be particularly suitable for use in systems allowing the analysis of biological matrices such as the skin.

In addition, unlike the methods of the prior art operating at pH 2 and temperatures above 50°, the methods for analyzing matrices according to the disclosure using at least one compound AB according to the disclosure make it possible to obtain stable analyses at body pH and temperatures (pH between 5 and 8, and T° between 23° C. and 40° C.), making the use of such compounds particularly effective for in vivo analyses such as for example on the skin, but also for performing stable analyses on biological specimens taken from samples, without the risk of damaging the specimen during the analysis.

Compounds A and B according to the disclosure have the advantage of offering a potential difference close to that of the skin, which is both high enough to be observable (at least 20 mV of potential difference between compound A and the corresponding compound B), and low enough to avoid creating a danger for the skin. Thus, the compounds AB prove to be particularly suitable for carrying out electrochemical analyses on the skin.

Compounds A and B according to the disclosure also have the advantage of causing a change in color depending on the oxidation state of the matrix, without adding colored indicators. This makes compounds A and B particularly suitable for spectrophotometric analyses. In addition, as it is not necessary to add a colored indicator, which is often toxic, the compounds AB are particularly suitable for analysis by spectrophotometry in systems comprising biological matrices.

Finally, the compounds AB according to the disclosure also have the advantage of being visible in fluorescence spectroscopy (fluorimetry) without having to add a fluorescent compound. This makes compounds AB particularly suitable for analyses by fluorimetry.

The disclosure also has the advantage of making it possible to measure different total antioxidant/oxidizing powers corresponding to different instants t, and to achieve the corresponding kinetics.

Thus, measuring the total antioxidant/oxidizing power, or even the oxidative score, makes it possible to monitor oxidative stress in order to detect and prevent possible pathologies; it also makes it possible to monitor the effectiveness and safety of a treatment and its timely adjustments, as well as optimizing the formulation and manufacture of pharmaceuticals, cosmetics, food and nutraceuticals.

BRIEF DESCRIPTION OF THE DRAWINGS

FIG. 1 shows an electrochemical curve obtained after 10 minutes of recording using a mediator system as described herein with microelectrodes applied to the skin.

DETAILED DESCRIPTION

A first object of the disclosure relates to the use of at least one compound AB chosen from NADH, NADPH, Cyt C (Fe2+) or $H_2O_2$ for measuring the status of oxidative stress of a biological matrix, characterized in that the at least one compound is available in two forms A and B that do not interact with each other, and that are capable of interacting and/or forming complexes respectively with an antioxidant and an oxidant present on the surface or in the biological matrix.

In a first embodiment of the disclosure, a single compound AB is used to measure the status of oxidative stress. This compound AB can be any of the compounds NADH, NADPH, Cyt C (Fe2+) or $H_2O_2$.

In a second embodiment of the disclosure, at least two compounds AB are used simultaneously. It is, therefore, possible to use 2, 3 or all 4 compounds AB according to the disclosure. Combining two or more compounds AB within the same measuring medium can be advantageous to make it possible to increase the sensitivity of the measurement (detection thresholds) and, therefore, the reliability of the method for determining oxidative stress.

For example, it is possible to use a group A comprising two compounds $NAD^+$ (0.1 M) and Cyt C $Fe^{3+}$ (0.15 M) and a group B comprising two compounds NADH (0.1 M) and Cyt $Fe^{2+}$ (0.15 M) to measure the antioxidant/oxidizing power of the biological matrix.

The compounds AB according to the disclosure are available in two forms, A and B, that do not interact with each other, and that are capable of interacting and/or of forming complexes respectively with an antioxidant and an oxidant present at the surface or in the biological matrix.

The term "compound AB" or "mediator AB" according to the disclosure is understood to mean at least one compound chosen from NADH, NADPH, Cyt C ($Fe^{2+}$) or $H_2O_2$.

This mediator AB has the advantage of dissociating in two forms:
- on the one hand, a compound A, which represents the "oxidizing" form, comprising at least one compound from among NADH, NADPH, Cyt C ($Fe^{2+}$) or $H_2O_2$; this compound will attract antioxidant molecules, but does not react with compound B, which represents the "antioxidant" form of mediator AB;
- on the other hand, a compound B, which represents the "antioxidant" form, will attract oxidizing molecules (also called free radicals) to itself, but does not react with the compound of form A, which represents the "oxidant" form of compound AB.

The compounds AB according to the disclosure are provided in forms A and B as presented in Table 1.

TABLE 1

Presentation of forms A and B of compounds AB according to the disclosure.

| Mediator | Mediator NADH | Mediator NADPH | Cyt C mediator ($Fe^{2+}$) | Mediator $H_2O_2$ |
|---|---|---|---|---|
| Form A "oxidant" | NAD+ | NADP | Cyt C($Fe^{3+}$) | $HO^-$ |
| Form B "antioxidant" | NADH | NADPH | Cyt C($Fe^{2+}$) | $H_2O_2$ |

Thus, the two different states A and B of groups AB do not balance each other; they balance only in contact with the oxidizing and antioxidant molecules of the matrix, which guarantees the accuracy of the measurement carried out, which will not be distorted by interactions between A and B.

The term "biological matrix" is understood to mean a matrix originating from the field of living organisms. Such a matrix can come from a sample (example: blood, urine, sweat, hair, seminal and follicular fluids, etc.), or concern a part of a living organism (example: a tissue such as the skin, etc.).

The term "status of oxidative stress" is understood to mean the balance between oxidants and antioxidants in the matrix to be analyzed. This status indicates whether the matrix is mainly made up of oxidizing molecules, mainly made up of antioxidant molecules, or in balance between antioxidants and oxidants.

The term "measurement of the status of oxidative stress" is understood to mean the measurement of the electrochemical potential, of the absorbance by spectrophotometry or of the intensity of the fluorescence by fluorimetry to obtain one of the following parameters: total antioxidant/oxidizing power, anti-free radical effect, reducing effect or protective effect, in order to deduce a general status concerning the state of oxidative stress of the matrix.

The term "anti-free radical effect" is understood to mean the capacity of a substance to inhibit by trapping, by the "scavaging" effect, the free radicals present in the medium.

The term "reducing effect" is understood to mean the ability of a substance to donate electrons by reducing the free radicals present in the medium.

The term "protective effect" is understood to mean the ability of a substance to protect itself, by sacrificing itself, against the presence of free radicals in the medium. The status of oxidative stress can take the form of a numerical value scale for which the:
- Lowest values correspond to the case where there is little or no oxidative stress
- Intermediate values correspond to the case where oxidative stress can lead to risks for the biological matrices.
- High values correspond to severe oxidative stress.

The term "total antioxidant/oxidizing power" is understood to mean the ratio between the total antioxidizing power and the total oxidizing power. Thus, total antioxidant/oxidizing power can also be written as total antioxidizing power/total oxidizing power or even the ratio of total antioxidant/oxidizing power.

The total antioxidant/oxidizing power of the matrix is positively correlated with the status of oxidative stress of the matrix.

Thus, a high total antioxidant/oxidizing power corresponds to an imbalance of the antioxidant/oxidant balance in favor of an increased presence of antioxidant molecules and, therefore, corresponds to a status of oxidative stress: "no or little oxidative stress."

Conversely, a low total antioxidant/oxidizing power corresponds to an imbalance of the antioxidant/oxidant balance in favor of an increased presence of oxidant molecules and, therefore, corresponds to a status of oxidative stress: "severe oxidative stress."

The anti-free radical effect of the matrix is negatively correlated with the status of oxidative stress of the matrix. Thus, a high anti-free radical effect corresponds to an increased presence of antioxidant molecules and, therefore, corresponds to a status of oxidative stress: "no or little oxidative stress." Conversely, a low anti-free radical effect corresponds to an imbalance of the antioxidant/oxidant balance in favor of an increased presence of oxidant molecules and, therefore, corresponds to the status of oxidative stress: "severe oxidative stress."

The reducing effect of the matrix is negatively correlated with the status of oxidative stress of the matrix. Thus, a high reducing effect corresponds to an imbalance of the antioxidant/oxidant balance in favor of the increased presence of antioxidant molecules and, therefore, corresponds to a status of oxidative stress: "no or little oxidative stress." Conversely, a low reducing effect corresponds to an imbalance of the antioxidant/oxidant balance in favor of an increased presence of oxidant molecules and, therefore, corresponds to the status of antioxidant/oxidative stress: "severe oxidative stress."

The protective effect of the matrix is negatively correlated with the status of oxidative stress of the matrix. Thus, a high protective effect corresponds to an imbalance of the antioxidant/oxidant balance in favor of the increased presence of antioxidant molecules and, therefore, corresponds to a status of oxidative stress: "no or little oxidative stress." Conversely, a low protective effect corresponds to an imbalance of the antioxidant/oxidant balance in favor of an increased presence of oxidant molecules and, therefore, corresponds to the status of oxidative stress: "severe oxidative stress."

A second object of the disclosure relates to a device for measuring the total antioxidant/oxidizing power of a biological matrix comprising a measuring medium in which are immersed one or more working electrodes and several reference electrodes, characterized in that the medium comprises at least one compound AB available in two forms A and B, which are capable of interacting and/or of forming complexes respectively with antioxidants and oxidants present at the surface or in the matrix, and not interacting with each other, and in that the at least one compound AB is chosen from NADH, NADPH, Cyt C ($Fe^{2+}$) or $H_2O_2$.

Within the meaning of the disclosure, the term "electrode" is understood to mean an electronic or ionic conductor picking up electrons.

The device for measuring the total antioxidant/oxidizing power of the matrix comprises two kinds of electrodes. On the one hand there are the reference electrode(s), the potential of which does not vary during the measurements, and on the other hand there are the working electrode(s), the potential difference of which will be measured with respect to the reference electrode.

In a preferred embodiment of the disclosure, the electrodes are made of metal.

Regarding the working electrodes, there can be either a single working electrode, which is a complex electrode, or several working electrodes (not complex).

In a preferred embodiment, the electrodes are composed of a mixture of metal. The term "mixture of metal" is understood to mean either a combination of metals within a single electrode, or the use of different metals each forming a part of an electrode considered as a whole.

In a preferred embodiment, the device contains only one working electrode, which is a complex working electrode.

The term "complex working electrode" is understood to mean an electrode made up of at least two materials chosen from among gold, platinum or tungsten.

In a particular embodiment, the working electrode is a complex electrode made up of a mixture of tungsten, platinum and gold. Such an electrode can for example consist of 60% gold, 10% platinum and 30% tungsten or 50% gold, 27% platinum and 33% tungsten. In another particular embodiment, the reference electrode is made of Ag+/Ag (silver chloride electrode).

In a preferred embodiment, the reference electrode is made of Ag+/Ag and the working electrode is a mixture of tungsten, platinum and gold.

The term "measurement of the total antioxidant/oxidizing power" is understood to mean the measurement of the ratio between the total antioxidant power and the total oxidizing power. This measurement is carried out mainly by measuring the electrochemical potential of the measuring medium.

Measuring the total antioxidant/oxidizing power makes it possible to monitor oxidative stress in order to detect and prevent possible pathologies; it also makes it possible to monitor the effectiveness and safety of a treatment and its timely adjustments, as well as optimizing the formulation and manufacture of pharmaceuticals, cosmetics, food and nutraceuticals.

The present device is characterized by the fact that the means for measuring the antioxidant/oxidizing power consists of a means for measuring the electrochemical potential of the measuring medium, the latter incorporating at least one compound AB present in two forms A and B, which are suitable for reacting and/or forming a complex respectively with the antioxidant and oxidizing species present at the surface or in the matrix, so as to modify the electrochemical potential of the measuring medium.

The compounds AB according to the disclosure have the advantage of offering a potential difference close to that of the skin, which is both high enough to be observable (at least 20 mV of potential difference between A and B), and low enough to avoid creating a danger for the biological matrix. Thus, the mediator AB proves to be particularly suitable for analyses by electrochemistry.

The term "measuring medium," which can also be called a mediator system, is understood to mean any medium that can be used to carry out a measurement of the total antioxidant/oxidizing power of the matrix.

In a preferred embodiment of the disclosure, the measuring medium is in liquid or gelled form.

In an even more preferred embodiment, the liquid or gelled measuring medium is a solution composed of KCl. Such a composition makes it possible to stabilize the measurement. In addition, and importantly, it is compatible with the biological matrices. In a preferred embodiment, the KCl solution is at a concentration between 0.5 and 2.5 mmol/L.

The specificity of the measuring media according to the disclosure is that they always contain at least one compound AB according to the disclosure. In a particular embodiment, the measuring medium is in liquid form. A liquid measuring medium is particularly useful for measuring the total antioxidant/oxidizing power of liquid biological matrices such as blood or urine. In another alternative embodiment, the measuring medium is in gelled form. A gelled measuring medium is particularly useful for measuring the total antioxidant/oxidizing power at the surface of biological matrices such as the skin.

A third object of the disclosure relates to a method for measuring the status of oxidative stress of a biological matrix comprising the steps of:

bringing the matrix into contact with a measuring medium comprising at least one compound AB chosen from NADH, NADPH, Cyt C ($Fe^{2+}$) or $H_2O_2$, available in two forms A and B that are capable of interacting and/or forming complexes respectively with an antioxidant and an oxidant present at the surface or in the matrix, measuring the electrochemical potential between a complex working electrode or several working electrodes and one or more reference electrodes placed on the matrix by electrochemistry, or measuring a variation in the absorbance by spectrophotometry.

Advantageously, the mediator medium according to the disclosure comprises at least one compound AB, and allows measurement by electrochemistry, by spectrophotometry or by fluorimetry, without having to add reagents specific to the measurement method into the medium.

In one embodiment of the disclosure, the measuring medium is in liquid or gelled form.

In another preferred embodiment, the liquid or gelled measuring medium is made up in particular of a KCl solution. Such a composition makes it possible to stabilize the measurement. In a preferred embodiment, the KCl solution is at a concentration between 0.5 and 2.5 mmol/L. \The matrix can be brought into contact with a measuring medium:
- In the case where the matrix to be tested is solid, by applying a gelled measuring medium to the surface of the matrix; this method of bringing into contact is in particular useful for carrying out analyses of the "in vivo" type directly on a tissue such as for example the skin.
- In the case where the matrix to be tested is liquid, by dissolving the matrix in a liquid mediating medium; this method of bringing into contact is in particular useful for carrying out analyses on iological specimens such as blood or urine.

By way of example, for a blood sample, the measurement is carried out by placing 200 µl of blood in a volume of 2.5 mL of mediator system.

The term "measurement of the status of oxidative stress" is understood to mean the measurement of the electrochemical potential, of the absorbance by spectrophotometry or of the intensity of the fluorescence by fluorimetry, of one of the following parameters: total antioxidant/oxidizing power, anti-free radical effect, reducing effect or protective effect of a matrix in order to deduce a general status therefrom concerning the state of oxidative stress of the matrix.

In a particular embodiment of the disclosure, the method is characterized in that the means for measuring the status of oxidative stress consists of a means for measuring the total antioxidant/oxidizing power of the matrix, based on the analysis of the electrochemical potential of the measuring medium. The latter incorporating at least one compound AB present in two forms A and B, which are capable of reacting and/or of forming a complex respectively with the antioxidant and oxidizing species present at the surface or in the matrix, so as to modify the electrochemical potential of the measuring medium.

The use of two groups of compounds AB according to the disclosure in an electrochemical measurement has the advantage of offering a potential difference close to that of the skin, which is both high enough to be observable (at least 20 mV of potential difference between group A and group B), and low enough so as not to create a danger for the biological matrix. Thus, the compound AB proves to be particularly suitable for carrying out analyses by electrochemistry.

Measuring the electrochemical potential also makes it possible to analyze the effect of a product on a biological matrix; to this end, the difference is calculated between the value of the difference in potential between the electrodes or the complex working electrode and the reference electrode(s) taken at t0 and the value of the difference in potential between these same electrodes taken at an instant t to be tested. The instant t0 corresponds to a moment before the setting or the action of the product whose effect on the biological matrix is to be verified. It is thus possible to measure different total antioxidant/oxidizing powers corresponding to different instants t, and to achieve the corresponding kinetics.

In an alternative embodiment of the disclosure, the method is characterized in that the means for measuring the status of oxidative stress consists of a means for measuring the anti-free radical effect and the reducing effect of the matrix, based on the study of the absorbance of the measuring medium. The latter incorporating at least one compound AB present in two forms A and B, which are capable of reacting and/or forming complexes respectively with the antioxidant and oxidizing species present at the surface or in the matrix, so as to modify the absorbance value of the measuring medium.

Using at least one compound AB according to the disclosure has the advantage of causing a change in color of the medium depending on the oxidation state of the matrix brought into contact with it, without adding any colored indicators. This makes compounds AB particularly suitable for spectrophotometric analyses. In addition, as it is not necessary to add a colored indicator, which is often toxic, the compounds AB are particularly suitable for analysis by spectrophotometry in systems comprising biological matrices.

Spectrophotometry also makes it possible to analyze the effect of a product on a biological matrix; to do this, the difference is calculated between the value of the absorbance at t0 and the value of the absorbance at an instant t to be tested. The instant t0 corresponds to a moment before the setting of the product whose effect on the biological matrix is to be verified. It is thus possible to measure different anti-free radical and reducing effects, corresponding to different instants t, and to achieve the corresponding kinetics.

In an alternative embodiment of the disclosure, the method is characterized in that the means for measuring the status of oxidative stress consists of a means for measuring the fluorescence of the measuring medium, the latter incorporating at least one compound AB present in two forms A and B, which are capable of reacting and/or of forming complexes respectively with the antioxidant and oxidizing species present at the surface or in the matrix, so as to modify the value of the fluorescence of the measuring medium.

In an advantageous embodiment, measuring the status of oxidative stress also makes it possible to analyze the effect of a product on a biological matrix; to do this, the difference is calculated between the value of the status of the oxidative stress at t0 and the value at an instant t to be tested.

The instant t0 corresponds to a moment before the setting or the action of the product whose effect on the biological matrix is to be verified. It is thus possible to measure different statuses of the oxidative stress corresponding to different instants t, and to achieve the corresponding kinetics. Studying the kinetics of the status of oxidative stress is particularly useful for determining the effect of a product on the antioxidant/oxidant balance of the biological matrix over time.

A fourth object of the disclosure relates to a method for determining the oxidative score of a biological matrix comprising the combination of the results of at least two measurements chosen from:
- an electrochemical measurement measuring the total antioxidant/oxidizing power of the matrix by applying a method comprising bringing the matrix into contact with a measuring medium comprising at least one compound AB chosen from NADH, NADPH, Cyt C ($Fe^{2+}$) or $H_2O_2$, available in two forms A and B which are capable of interacting and/or forming complexes respectively with an antioxidant and an oxidant present at the surface or in said matrix, wherein the measuring medium is in liquid form or in gelled form, a spectrophotometric measurement measuring the anti-free radical effect and the reducing effect of the matrix, and a measurement by fluorimetry measuring the protective effect of the matrix.

In a particular embodiment, at least two compounds AB are used simultaneously.

The oxidative score is an index providing information on the oxidizing state of the biological matrix. It provides an indication of the number of free radicals present in the biological matrix. It is obtained through the "measurement of the total antioxidant/oxidizing power,"

$$\text{Oxidative score} = \left(\frac{EP_{Skin10} - EP_{control\,t0}}{EP_{control\,t0}}\right) \times 100$$

The status of oxidative stress is an index providing precise information on the antioxidant and oxidizing state of the biological matrix. It represents the degree of oxidative stress (the balance between antioxidants and oxidants). The oxidative score is calculated by combining the measurement of the total antioxidant/oxidizing power, the anti-free radical effect, the reducing effect and the protective effect.

Status of oxidative stress=100−[(anti−free radical effect+reducing effect+protective effect)−oxidative score]

The Oxidative Index differs from the status of oxidative stress in that it is based on at least two informative parameters concerning the oxidative stress of the matrix, obtained by at least two different measuring methods. Using two different measurement methods chosen from electrochemistry, spectrophotometry or fluorimetry makes it possible to refine the precision of the index.

As stated above, each measuring method will make it possible to measure one or more different parameters. Manufacturers have often played on this multiplicity of parameters to highlight the parameter that benefits them the most in the eyes of customers.

The oxidative score makes it possible to avoid this kind of bias by combining the results of different parameters from different measurements into a single score, thus offering a clear indication of the oxidative state of the biological matrix while offering better guarantees as to the relevance of the result.

In a preferred embodiment of the disclosure, the oxidative score is calculated by combining the measurement of the total antioxidant/oxidizing power, the anti-free radical effect, the reducing effect and the protective effect. Such an oxidative score offers the most precise measurement of the oxidative state of the biological matrix because it combines a large number of parameters relating to the oxidative state of the biological matrix.

In a specific embodiment, the measurement of the oxidative score also makes it possible to analyze the effect of a product on a biological matrix; for this purpose, the difference is calculated between the value of the oxidative score taken at t0 and the value taken at an instant t to be tested. The instant t0 corresponds to a moment before the setting or the action of the product whose effect on the biological matrix is to be verified. It is thus possible to measure different oxidative scores corresponding to different instants t, and to achieve the corresponding kinetics.

Studying the kinetics of the oxidative score is particularly useful for determining the effect of a product on the oxidative state of the biological matrix over time.

EXAMPLES

Example 1: Measurement of the Status of Oxidative Stress

The status of oxidative stress is measured on the skin (forearm) of a 26-year-old woman who has fasted for 12 hours before the measurement, at a temperature and humidity of respectively (20° C.<T<23° C. and 50%<RH<60%).

Before the analysis, the skin was washed with water and dried with absorbent paper (the surface of the analysis is 2 cm2).

The device is made up of:

A gelled mediator system comprising the NADH mediator compound according to the disclosure (dissociating into two forms NAD+ and NADH respectively reacting with an antioxidant and an oxidant and not reacting with each other) as well as a solution of KCl at a concentration of 2 mmol/L.

Microelectrodes attached to the arms, in contact with the mediator system: a reference electrode made from silver, and a working electrode made from Gold (50%), platinum (27%) and tungsten (33%).

The status of oxidative stress is observed by measuring the total antioxidant/oxidizing power.

The measurement of the total antioxidant/oxidizing power consists of electrochemical monitoring of the changes in the concentration of the oxidized (NAD+) and reduced (NADH) forms of the mediator (NADH) during the reaction with the antioxidants and oxidants present in the matrix.

FIG. 1 shows the electrochemical curve obtained after 10 minutes of recording using the mediator system and the microelectrodes applied to the skin.

The total oxidizing power and the total antioxidizing power are measured according to the following formulas:

$$\text{Total oxidizing power} = \left(\frac{EP_{Skin10} - EP_{control\,t0}}{EP_{control\,t0}}\right) \times 100 = 3.12$$

$$\text{Total antioxidizing power} = \left(\frac{EP_{Skin10} - EP_{Skin\,3\,min}}{EP_{Skin\,3\,min}}\right) \times 100 = 15.62$$

Where $EP_{skin10}$ corresponds to the electrochemical potential measured at time 10 min.

$EP_{control\,t0}$ corresponds to the electrochemical potential measured at time to.

And $EP_{skin\,3\,min}$ corresponds to the highest electrochemical potential.

The total antioxidant/oxidizing power is equal to the total antioxidizing power divided by the total oxidizing power, i.e., 15.62/3.12=5.00

The total antioxidant/oxidizing power of the patient's skin is, therefore, 5.00.

The patient, therefore, has an oxidative stress status value of 5.00; this corresponds to the case where there is very little oxidative stress.

The invention claimed is:

1. A device for measuring a total antioxidant/oxidizing power of a biological matrix comprising a measuring medium in which are immersed one or more working electrodes and one or more reference electrodes, wherein the one or more working electrodes is a complex working electrode consisting essentially of a mixture of 50% gold, 27% platinum, and 33% tungsten or of 60% gold, 10% platinum, and 30% tungsten, and wherein the measuring medium comprises at least one compound available in two forms, which are capable of interacting and/or of forming complexes respectively with antioxidants and oxidants present at a surface or in the biological matrix, and not interacting with each other, and wherein the at least one compound is chosen from NADH, NADPH, Cyt C ($Fe^{2+}$) or $H_2O_2$.

2. The device of claim 1, wherein the one or more reference electrodes comprises silver chloride.

3. The device of claim 2, wherein the measuring medium comprises a solution of potassium chloride.

4. The device of claim 1, wherein the measuring medium comprises a solution of potassium chloride.

5. A method for measuring a status of an oxidative stress of a biological matrix, comprising:
   using at least one compound that is non-toxic to a skin chosen from NADH, NADPH, Cyt C ($Fe^{2+}$) or $H_2O_2$ for measuring the status of the oxidative stress of the biological matrix, wherein the at least one compound is available in two forms that do not interact with each other, and the two forms are capable of interacting and/or forming complexes respectively with an antioxidant and an oxidant present on a surface of the biological matrix or in the biological matrix; and
   using the device according to claim 1, contacting the complex working electrode with the biological matrix, and measuring an electrochemical potential between the complex working electrode and the one or more reference electrodes.

6. The method of claim 5, wherein using the at least one compound that is non-toxic to the skin chosen from NADH, NADPH, Cyt C ($Fe^{2+}$) or $H_2O_2$ for measuring the status of oxidative stress of the biological matrix comprises simultaneously using at least two compounds that are non-toxic to the skin and chosen from NADH, NADPH, Cyt C ($Fe^{2+}$) or $H_2O_2$ for measuring the status of oxidative stress of the biological matrix.

7. A method for measuring a status of oxidative stress of a biological matrix, comprising the steps of:
   bringing the biological matrix into contact with a measuring medium comprising at least one compound chosen from NADH, NADPH, Cyt C ($Fe^{2+}$) or $H_2O_2$, available in two forms that are capable of interacting and/or forming complexes respectively with an antioxidant and an oxidant present at a surface of the biological matrix or in the biological matrix; and
   using the device according to claim 1 and measuring an electrochemical potential between the complex working electrode and the one or more reference electrodes while the complex working electrode is in contact with the biological matrix.

8. The method of claim 7, wherein the measuring medium is in liquid form or in gelled form.

9. The method of claim 8, wherein the measuring medium simultaneously comprises at least two compounds chosen from NADH, NADPH, Cyt C ($Fe^{2+}$) or $H_2O_2$, each of the at least two compounds available in two forms that are capable of interacting and/or forming complexes respectively with the antioxidant and the oxidant present at the surface of the biological matrix or in the biological matrix.

10. A method for determining an oxidative score of a biological matrix, comprising combining results of at least two measurements chosen from:
    electrochemical measurement measuring a total antioxidant/oxidizing power of the biological matrix by applying the method according to claim 7;
    a spectrophotometric measurement measuring an anti-free radical effect and a reducing effect of the biological matrix; and
    a measurement by fluorimetry measuring a protective effect of the biological matrix.

11. The method of claim 10, further comprising measuring a total antioxidant/oxidizing power of the anti-free radical effect of the biological matrix, measuring the reducing effect of the biological matrix, and measuring the protective effect of the biological matrix.

* * * * *